United States Patent
Neitz et al.

(10) Patent No.: US 12,403,325 B2
(45) Date of Patent: Sep. 2, 2025

(54) LIGHTING DEVICES, SYSTEMS, METHODS FOR STIMULATING CIRCADIAN RHYTHMS

(71) Applicant: University of Washington, Seattle, WA (US)

(72) Inventors: Jay Neitz, Seattle, WA (US); Maureen Neitz, Seattle, WA (US); James A. Kuchenbecker, Seattle, WA (US); Sara S. Patterson, Seattle, WA (US); Alexandra Neitz, Seattle, WA (US)

(73) Assignee: University of Washington, Seattle, WA (US)

( * ) Notice: Subject to any disclaimer, the term of this patent is extended or adjusted under 35 U.S.C. 154(b) by 638 days.

(21) Appl. No.: 17/612,061

(22) PCT Filed: May 20, 2020

(86) PCT No.: PCT/US2020/033844
§ 371 (c)(1),
(2) Date: Nov. 17, 2021

(87) PCT Pub. No.: WO2020/236958
PCT Pub. Date: Nov. 26, 2020

(65) Prior Publication Data
US 2022/0203118 A1    Jun. 30, 2022

Related U.S. Application Data

(60) Provisional application No. 62/850,493, filed on May 20, 2019.

(51) Int. Cl.
*A61N 5/06* (2006.01)
*A61M 21/00* (2006.01)
(Continued)

(52) U.S. Cl.
CPC ... *A61N 5/0618* (2013.01); *A61M 2021/0044* (2013.01); *A61N 2005/0652* (2013.01);
(Continued)

(58) Field of Classification Search
CPC .......... A61N 5/0618; A61N 2005/0652; A61N 2005/0662; A61M 2021/0044
See application file for complete search history.

(56) References Cited

U.S. PATENT DOCUMENTS 4,176,299 A * 11/1979 Thornton, Jr. ..... C09K 11/7739
                                                        257/E25.02
6,114,503 A    9/2000 Wei
(Continued)

FOREIGN PATENT DOCUMENTS

WO    2018212819    11/2018

OTHER PUBLICATIONS

Aschoff, Jurgen, and R. Ü. T. G. E. R. Wever. "Human circadian rhythms: a multioscillatory system." Federation proceedings. vol. 35. No. 12. 1976. pp. 2326-2332.
(Continued)

*Primary Examiner* — Catherine M Voorhees
(74) *Attorney, Agent, or Firm* — Christensen O'Connor Johnson Kindness PLLC

(57) ABSTRACT

Lighting devices, systems, and methods for selectively activating S cones and L+M cones in a human retina and for regulating the phase of circadian rhythm in a human subject.

14 Claims, 6 Drawing Sheets

(51) Int. Cl.
    *F21Y 107/30* (2016.01)
    *F21Y 115/10* (2016.01)
(52) U.S. Cl.
    CPC ... *A61N 2005/0662* (2013.01); *F21Y 2107/30* (2016.08); *F21Y 2115/10* (2016.08)

(56) References Cited

U.S. PATENT DOCUMENTS

| | | | | |
|---|---|---|---|---|
| 2006/0106437 | A1* | 5/2006 | Czeisler | A61M 21/02 607/88 |
| 2014/0265937 | A1* | 9/2014 | Maxik | A61M 21/00 315/360 |
| 2014/0306620 | A1* | 10/2014 | Maxik | A61M 21/00 315/294 |
| 2017/0238401 | A1 | 8/2017 | Sadwick | |
| 2017/0348506 | A1 | 12/2017 | Berman | |
| 2018/0317296 | A1* | 11/2018 | Chen | H05B 45/20 |

OTHER PUBLICATIONS

Berson, David M., Felice A. Dunn, and Motoharu Takao. "Phototransduction by retinal ganglion cells that set the circadian clock." Science 295.5557 (2002): 1070-1073.
Brainard, George C., et al. "Action spectrum for melatonin regulation in humans: evidence for a novel circadian photoreceptor." Journal of Neuroscience 21.16 (2001): 6405-6412.
Brouwer, A., et al. "Light therapy: is it safe for the eyes?" Acta Psychiatrica Scandinavica 136.6 (2017): 534-548.
Crowley, Stephanie J., and Charmane I. Eastman. "Phase advancing human circadian rhythms with morning bright light, afternoon melatonin, and gradually shifted sleep: can we reduce morning bright-light duration?" Sleep medicine 16.2 (2015): 1-27.
Czeisler, Charles A., et al. "Bright light resets the human circadian pacemaker independent of the timing of the sleep-wake cycle." Science 233.4764 (1986): 667-671.
Czeisler, Charles A., et al. "Entrainment of Human Circadian Rhythms by Light-Dark Cycles: A Reassessment." Photochemistry and photobiology 34.2 (1981): 239-247.
Dacey, Dennis M., et al. "Melanopsin-expressing ganglion cells in primate retina signal colour and irradiance and project to the LGN." Nature 433.7027 (2005): 749-754.
De La Iglesia, Horacio O., et al. "Access to electric light is associated with shorter sleep duration in a traditionally hunter-gatherer community." Journal of biological rhythms 30.4 (2015): 1-15.

DeCoursey, Patricia J. "Phase control of activity in a rodent." In Cold Spring Harbor Symposia on Quantitative Biology. Cold Spring Harbor Laboratory Press. vol. 25. 1960. pp. 49-55.
Hattar, Samer, et al. "Melanopsin-containing retinal ganglion cells: architecture, projections, and intrinsic photosensitivity." Science 295.5557 (2002): 1-10.
St Hilaire, Melissa A., et al. "Human phase response curve to a 1 h pulse of bright white light." The Journal of physiology 590.13 (2012): 3035-3045.
Khalsa, Sat Bir S., et al. "A phase response curve to single bright light pulses in human subjects." The Journal of physiology 549.3 (2003): 945-952.
Khan, Suliman, et al. "Health risks associated with genetic alterations in internal clock system by external factors." International journal of biological sciences 14.7 (2018): 791-798.
LeGates, Tara A., et al. "Aberrant light directly impairs mood and learning through melanopsin-expressing neurons." Nature 491 (2012): 594-598.
Lewy, Alfred J., et al. "Antidepressant and circadian phase-shifting effects of light." Science 235.4786 (1987): 352-354.
Lewy, Alfred J., et al. "Light suppresses melatonin secretion in humans." Science 210.4475 (1980): 1267-1269.
Lucas, Robert J., et al. "Measuring and using light in the melanopsin age." Trends in neurosciences 37.1 (2014): 1-17.
Masland, Richard H. "The neuronal organization of the retina." Neuron 76.2 (2012): 1-28.
Revell, Victoria L., Thomas A. Molina, and Charmane I. Eastman. "Human phase response curve to intermittent blue light using a commercially available device." The Journal of physiology 590.19 (2012): 4859-4868.
Roenneberg, Till, et al. "Light and the human circadian clock." In Handbook of Experimental Pharmacology. 2013. 29 pages.
Ruger, Melanie, et al. "Human phase response curve to a single 6.5 h pulse of short-wavelength light." The Journal of physiology 591.1 (2013): 353-363.
Wright Jr, Kenneth P., et al. "Entrainment of the human circadian clock to the natural light-dark cycle." Current Biology 23.16 (2013): 1-14.
International Preliminary Report on Patentablility mailed Nov. 16, 2021, issued in corresponding International Application No. PCT/US2020/033844, filed May 20, 2020, 10 pages.
International Search Report mailed Sep. 23, 2020, issued in corresponding International Application No. PCT/US2020/033844, filed May 20, 2020, 12 pages.

* cited by examiner

LIGHTING DEVICES, SYSTEMS, METHODS FOR STIMULATING CIRCADIAN RHYTHMS

CROSS-REFERENCE TO RELATED APPLICATION

This application is a US national stage application based on PCT/US2020/033844, filed May 20, 2020, which claims the benefit of U.S. Application No. 62/850,493, filed May 20, 2019, each expressly incorporated herein by reference in its entirety.

STATEMENT OF GOVERNMENT LICENSE RIGHTS

This invention was made with government support under Grant No. R01 EY027859, awarded by the National Eye Institute. The government has certain rights in the invention.

BACKGROUND OF THE INVENTION

Despite the advances in the development of light therapies for changing the phase of human circadian rhythms and for stimulating non-image forming visual pathways involved in mood, alertness, and cognitive performance a need exists for improved systems that are more effective and more practical for use in everyday, home, business, educational and healthcare settings. The present invention seeks to fulfill this need and provides further related advantages.

SUMMARY OF THE INVENTION

The present invention provides systems, methods, and devices for using multiple narrow band ranges of visible light which are modulated imperceptibly either spatially or temporally to increase the efficacy of light therapies for circadian rhythm shifts in humans.

In one aspect, the invention provides a method for selectively activating S cones and L+M cones in a human retina and regulating the phase of circadian rhythm.

In certain embodiments, the invention provides a method for selectively activating S cones and L+M cones in a human retina. In one embodiment, the method comprises:
(a) exposing a human retina to a first multi-band light consisting of a first band having a peak emission at 430 nm and a second band having a peak emission at 565 nm; and
(b) exposing the human retina to a second multi-band light consisting of a first band having a peak emission at 485 nm, a second band having a peak emission at 565 nm, and a third band having a peak emission at 630 nm.

In other embodiments, the invention provides a method for regulating the phase of circadian rhythm in a subject. In one embodiment, the method comprises:
(a) exposing a subject's retina to a first multi-band light consisting of a first band having a peak emission at 430 nm and a second band having a peak emission at 565 nm; and
(b) exposing the subject's retina to a second multi-band light consisting of a first band having a peak emission at 485 nm, a second band having a peak emission at 565 nm, and a third band having a peak emission at 630 nm.

In another aspect of the invention, lighting devices are provided.

In one embodiment, the invention provides a lighting device effective for the S+(L+M) retinal cone activation. In this embodiment, the lighting device comprises two light sources:
(a) a first light source that emits a first band of light having a peak emission at 430 nm; and
(b) a second light source that emits a second band of light having a peak emission at 565 nm.

In another embodiment, the invention provides a lighting device is effective for L+M retinal cone activation. In one embodiment, the lighting device comprises three light sources:
(a) a first light source that emits a first band of light having a peak emission at 485 nm;
(b) a second light source that emits a second band of light having a peak emission at 565 nm; and
(c) a third light source that emits a third band of light having a peak emission at 630 nm.

In another embodiment, the lighting device comprises four light sources:
(a) a first light source that emits a first band of light having a peak emission at 430 nm;
(b) a second light source that emits a second band of light having a peak emission at 565 nm;
(c) a third light source that emits a third band of light having a peak emission at 485 nm; and
(d) a fourth light source that emits a fourth band of light having a peak emission at 630 nm.

In a further aspect, the invention provides lighting systems.

In certain embodiments, the invention provides a lighting system comprising:
(a) a first lighting device, comprising two light sources,
  (i) a first light source that emits a first band of light having a peak emission at 430 nm, and
  (ii) a second light source that emits a second band of light having a peak emission at 565 nm; and
(b) a second lighting device, comprising three light sources:
  (i) a first light source that emits a first band of light having a peak emission at 485 nm;
  (ii) a second light source that emits a second band of light having a peak emission at 565 nm; and
  (iii) a third light source that emits a third band of light having a peak emission at 630 nm.

In further aspects of the inventions, methods for selectively activating S cones and L+M cones in a human retina and methods for regulating the phase of circadian rhythm in a subject using the lighting devices and lighting systems are provided.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 2A shows the rise in saliva melatonin levels in individuals in the evening, which is regulated by an individual's internal circadian clock, and before and after one hour steady white light equated in intensity (dotted line shows a 1.2 minute advance). FIG. 2B compares rise in saliva melatonin levels in individuals in the evening after 1 hour of being subject to blue light (dotted line shows an 11 minute delay). FIG. 2C compares rise in saliva melatonin levels in individuals in the evening either after 1 hour of being subject to 430, 565 nm vs. 485, 565, 630 nm mode alternation (dotted line shows a +43 minute advance) in accordance with the present invention.

FIG. 3A is a schematic illustration of a single lighting element with circuitry to control four narrow bands of light with peak wavelengths near 430 nm, 485 nm, 565 nm and 630 nm. FIG. 3B is a representative system that combines individual lighting elements to create array structures to provide representative lighting panels of desired shapes and sizes. FIG. 3C illustrates a representative configuration of lighting elements combined in a cylindrical hexagonal shape (left image) for integration into a lighting fixture (left image) having a spherical shape (right image) that can be used as a table or floor lamp. FIG. 3D is a photograph of a single lighting element emitters for the different lighting bands are located at the center of an aluminum circuit board for dissipating heat.

DETAILED DESCRIPTION OF THE INVENTION

Figure 1A:
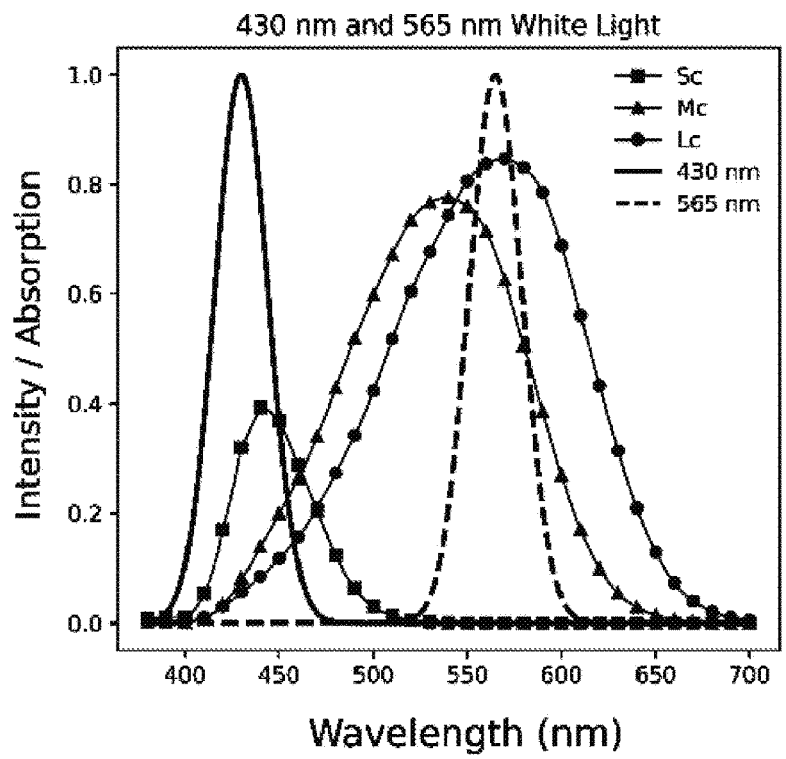
FIGS. 1A and 1B compares intensity distributions of lights from a representative lighting element (solid and dashed lines) with two different modes: 430, 565 nm mode (FIG. 1A) and 485, 565, 630 nm mode (FIG. 1B). Square, triangle, and circle lines show the absorption spectra of the human cones. The lighting element produces white light in either mode and the two modes can be adjusted to appear identical to human conscious perception.

Recent research has indicated that uptake of light by the retina of a mammalian eye includes subconscious responses to the activity of retinal ganglion cells with input circuitry from cone photoreceptors that imparts sensitivity to light with spatial and temporal properties and with spectral ranges previously not known (Patterson S S, Kuchenbecker J A, Anderson J R, Neitz M, Neitz J. A Color Vision Circuit for Non-Image-Forming Vision in the Primate Retina. Curr Biol. 2020 Apr. 6; 30(7):1269-1274.e2. doi: 10.1016/j.cub.2020.01.040.). The subconscious responses include aspects of the body's internal regulation, including, but not limited to the body's circadian rhythm. Previous study into the retina's uptake of blue wavelength light stimulation showed moderate response in terms of regulating the circadian rhythm. Presented herein are outcomes where complementary narrow bands are emitted, and combinations are used in alternating temporal and spatial fashion to present a mammalian body with visually perceptible white light that markedly impacts regulation of some functions (e.g., circadian rhythm, mood, alertness and cognitive function).

Methods for Selective Retinal Cone Activation and Regulating Circadian Rhythm

In one aspect, the invention provides a method for selectively activating S cones and L+M cones in a human retina and regulating the phase of circadian rhythm.

In certain embodiments, the invention provides a method for selectively activating S cones and L+M cones in a human retina. In one embodiment, the method comprises:
 (a) exposing a human retina to a first multi-band light consisting of a first band having a peak emission at 430 nm and a second band having a peak emission at 565 nm; and
 (b) exposing the human retina to a second multi-band light consisting of a first band having a peak emission at 485 nm, a second band having a peak emission at 565 nm, and a third band having a peak emission at 630 nm.

The bandwidth for each emission peak maximum is about 20 nm full-width at half maximum (FWHM).

The peak emission wavelength may have variance: 430 nm (± about 20 nm); 485 nm (± about 20 nm); 565 nm (±20 about nm); and 630 nm (± about 20 nm).

The first and second multi-band lights are nominally white because 430 nm and 560 nm lights are complementary colors and mixing complementary colors produces white. A mixture of 485 nm and 630 nm light is a violet color like the violet color of a 430 nm light and when mixed with yellow green 560 nm light also produces white. By adjusting the relative amounts of the different bands of light in each case it is possible to change the color temperature of the whites for different environment (e.g., people often prefer warm color temperatures of about 2700K for home lighting but daylight about 5000K might be preferred in an art gallery).

It will be appreciated that in the methods of the invention, the only lights used are the first and second multi-band light having the specified peak emissions. However, in certain embodiments, small amounts of additional wavelength bands can be added equally to both phases in order to optimize the exact color of the whites. Usually, color temperature of lights is varied along the "planckian locus" to make whites that are pleasing in color. If the whites produced by the prescribed wavelengths appears too green or too red, this can be adjusted by including some red or green wave bands to make subtle adjustments. The methods utilize the specified first and second multi-band light having the peak emission wavelengths as described herein.

In certain embodiments of the method, exposing the retina to the first multi-band light and the second multi-band light comprises alternating exposure to the retina at a frequency from about 10 to 30 Hz.

In other embodiments of the method, exposing the retina to the first multi-band light and the second multi-band light comprises exposure to one or more light sources emitting the first multi-band light and exposure to one or more light sources emitting the second multi-band light. In certain of these embodiments, the minimum number of light sources for each multi-band is two. In these embodiments, the number of light sources emitting the first multi-band light and the number of light sources emitting the second multi-band light are about equal. The luminance flux would be identical in modes where L+M cone activations are kept constant between the two modes. In (S+M)−L constant mode the two are similar in lumens but not identical.

In the practice of this aspect of the method of the invention, there are two modes where the first and second lights are alternated invisibly. In a first mode, L+M cone activation is kept constant between the first and second lights and only activation of S-cones is modulated between first and second lights. The transition between modes is imperceptible because S-cones are insensitive to temporal modulation. In a second mode, (S+M)−L cone activations are kept constant between the first and second lights. This can be imperceptible because conscious perception of blue vs. yellow is based on circuitry in the visual system that compares activation of (S+M) cones to L cones.

In other embodiments, the invention provides a method for regulating the phase of circadian rhythm in a subject. In one embodiment, the method comprises:
 (a) exposing a subject's retina to a first multi-band light consisting of a first band having a peak emission at 430 nm and a second band having a peak emission at 565 nm; and
 (b) exposing the subject's retina to a second multi-band light consisting of a first band having a peak emission at 485 nm, a second band having a peak emission at 565 nm, and a third band having a peak emission at 630 nm.

In certain embodiments, exposing the retina to the first multi-band light and the second multi-band light comprises alternating exposure to the retina at a frequency from about 15 to about 19 Hz.

In other embodiments, exposing the retina to the first multi-band light and the second multi-band light comprises exposure to one or more light sources emitting the first multi-band light and exposure to one or more light sources emitting the second multi-band light.

In certain embodiments of the methods described herein, the subject's retina is exposed to the first multi-band light and the second multi-band light for at least about 15 minutes to about 60 minutes per day (e.g., 20-30 minutes). In certain embodiments, exposure is for a full day (i.e., 8 hours). A minimum of 20 minutes in the morning while going through a normal routine, such as in the bathroom or kitchen, will help with social jet lag and reduce morning fatigue. At the other extreme, exposure for a full day, starting at home in the morning and then continuing throughout the productive part of the day at school or work until about 4 PM is anticipated to optimize circadian rhythms health and happiness. This would be like the experience of our prehistoric ancestors who lived outside and enjoyed a whole day of bright light exposure. However, in the late afternoon the lights should switch to "non-circadian disrupter mode" where the S-cone activation differential between the two modes is reduced to zero.

In the methods of the invention, the phase of circadian rhythm may be determined by measuring the subject's saliva melatonin levels. In certain embodiments, and as described herein, the subject's saliva melatonin levels are measured before and 12 hours after exposure to the first multi-band light and the second multi-band light.

Lighting Devices

In another aspect of the invention, lighting devices are provided.

In one embodiment, the invention provides a lighting device effective for the S+(L+M) retinal cone activation. In this embodiment, the lighting device comprises two light sources:
 (a) a first light source that emits a first band of light having a peak emission at 430 nm; and
 (b) a second light source that emits a second band of light having a peak emission at 565 nm.

In certain embodiments, the first and second bands of light are emitted from a single point source. In certain embodiments, the lighting device has a luminosity flux from about 200 to about 5000 lumens.

In another embodiment, the invention provides a lighting device is effective for L+M retinal cone activation. In this embodiment, the lighting device comprises three light sources:
 (a) a first light source that emits a first band of light having a peak emission at 485 nm;
 (b) a second light source that emits a second band of light having a peak emission at 565 nm; and
 (c) a third light source that emits a third band of light having a peak emission at 630 nm.

In certain embodiments, the first, second, and third bands of light are emitted from a single point source. In certain embodiments, the lighting device has a luminosity flux from about 200 to about 5000 lumens.

The lighting devices described herein are useful for implementing the methods of the invention. In certain embodiments, a single lighting device is capable of both modes and includes all four light sources (e.g., light-emitting devices, LEDS) 430 nm, 565 nm, 485 nm, and 630 nm. In these embodiments, the lighting device is a single light bulb or lighting element capable of temporally switching between modes. Also, individual elements could be incorporated into an array with half the elements in one mode and half in the other at any one moment. Each element includes the light sources (e.g., LEDS) at 430 nm, 565 nm, 485 nm, and 630 nm as active components but may also include light sources emitting at additional wavelengths where small amounts of light can be used to improve aesthetics or color rendering.

Thus, in another embodiment, the invention provides a lighting device, comprising four light sources:
 (a) a first light source that emits a first band of light having a peak emission at 430 nm;
 (b) a second light source that emits a second band of light having a peak emission at 565 nm;
 (c) a third light source that emits a third band of light having a peak emission at 485 nm; and
 (d) a fourth light source that emits a fourth band of light having a peak emission at 630 nm.

The lighting devices of the invention do not include any light source(s) other than specified above. The lighting devices do not include any other light source that emits light at a wavelength other than specified above. It will be appreciated that each light source's peak emission wavelength may have some variance (i.e., 430 nm (± about 20 nm); 485 nm (± about 20 nm); 565 nm (±20 about nm); and 630 nm (± about 20 nm)) and a bandwidth (full-width at half maximum about 20 nm).

It will be appreciated that in the lighting devices, the only lights used are the light bands having the specified peak emissions. However, in certain embodiments, small amounts of additional wavelength bands can be added equally to both phases in order to optimize the exact color of the white light.

Lighting System

In a further aspect of the invention, lighting systems are provided.

In certain embodiments, the invention provides a lighting system comprising:
 (a) a first lighting device, comprising two light sources,
  (i) a first light source that emits a first band of light having a peak emission at 430 nm, and
  (ii) a second light source that emits a second band of light having a peak emission at 565 nm; and
 (b) a second lighting device, comprising three light sources:
  (i) a first light source that emits a first band of light having a peak emission at 485 nm;
  (ii) a second light source that emits a second band of light having a peak emission at 565 nm; and
  (iii) a third light source that emits a third band of light having a peak emission at 630 nm.

In certain embodiments, the lighting system comprises two or more first lighting device and two or more second lighting devices. In certain of these embodiments, the lighting system comprises about the same number first lighting devices and second lighting devices.

In certain embodiments of the lighting system, L+M cone activation is kept constant between the first and second lighting devices and only activation of S-cones is temporally modulated between first and second lighting devices.

In other embodiments of the lighting system, (S+M)−L cone activations are kept constant between the first and second lighting devices.

As described above for the lighting devices, the lighting systems of the invention do not include any light source(s) other than specified above. The lighting systems do not include any other light source that emits light at a wavelength other than specified above. It will be appreciated that each light source's peak emission wavelength may have some variance (i.e., 430 nm (± about 20 nm); 485 nm (± about 20 nm); 565 nm (±20 about nm); and 630 nm (± about 20 nm)) and a bandwidth (full-width at half maximum about 20 nm).

It will be appreciated that in the lighting systems, the only lights used are the light bands having the specified peak emissions. However, in certain embodiments, small amounts of additional wavelength bands can be added equally to both phases in order to optimize the exact color of the white light.

The lighting system can be deployed in a low natural light environment or in an environment of a human subject in need of a phase shift to regulate the subject's circadian rhythm. All indoor lighting environments are examples where light intensities fall well short of direct-sunlight or cloud-covered sunlight intensities, such that they provide insufficient intensity to drive the circadian system effectively. Specific examples are artificial lighting for the home, commercial, industrial, medical, and classroom/school spaces. For example, homes—bedrooms, bathrooms, living rooms, kitchens; commercial—lobbies, stairways, offices, retail sales rooms, lounges, laboratories; industrial—cafeterias, work rooms, offices; Medical—patient rooms, nurses stations, day rooms; schools—classrooms, corridors, study halls, cafeterias.

The lighting systems can be used in the methods of the invention: a method for selectively activating S cones and L+M cones in a human retina; or a method for regulating the phase of circadian rhythm in a subject.

As noted above, in one aspect, the present invention includes methods, devices, and systems for manipulating circadian rhythms in humans. In certain embodiments, the devices and systems emit a first complementary multi-band white light (color temperature between 2700K and 5000K) that activates S-cones in the retina (a band having a maximum at about 430 nm) and that simultaneously actives L and M cones in the retina (a band having a maximum at about 565 nm). See FIG. 1A. In other embodiments, the devices and systems emit a second complementary multi-band light having band maxima at 485, 565, and 630 nm. See FIG. 1B. The multi-band light emits lights in narrow bandwidths specified by full width-at-half-maximum (FWHM) about each emission maximum. The approximate bandwidth for each emission peak is set forth in parentheses after each peak: 430 nm (20 nm±20 nm), 485 nm (25 nm±20 nm), 565 nm (30 nm±20) and 630 nm (35 nm±20 nm).

Figure 1B:
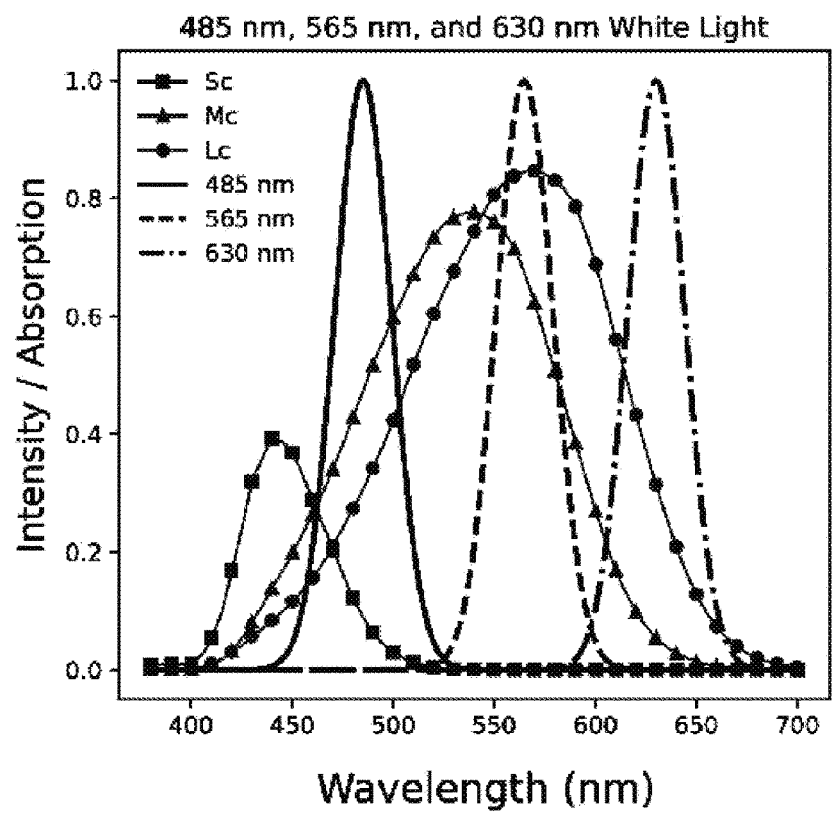

FIGS. 1A and 1B compare intensity distributions of lights from a representative lighting element (solid and dashed lines) with two different modes: 430, 565 nm mode (FIG. 1A) and 485, 565, 630 nm mode (FIG. 1B). Square-, triangle-, and circle-labeled lines show the absorption spectra of the human retinal cones (i.e., S-, M-, and L-cones, respectively). The lighting element produces white light (over a range of color temperatures between 2700K and 5000K) in either mode and the two modes can be adjusted to appear identical to human conscious perception. However, when the two modes are presented in either spatial or temporal alternation they powerfully but subconsciously stimulate ganglion cells in the retina of eye that regulate mood, arousal, cognitive performance and the phase of the circadian clock. This regulation is based on the very different activation of S vs. (L+M) cone activation between the modes (FIG. 1A, 430+565 nm, S+L+M; FIG. 1B, 485+565+630 nm, L+M only). Modulating S vs. L+M cone activation activates the newly discovered Color Vision Circuit for Non-Image-Forming Vision in the Primate Retina (Ref: Curr Biol. 2020 Apr. 6; 30(7):1269-1274.e2. doi: 10.1016/j.cub.2020.01.040). The two light sources can be presented in either spatial or temporal alternation. In the method of the invention, alternation of white light sources in space or time is not perceptible to human conscious vision change but it can be a powerful stimulus for intrinsically photosensitive retinal ganglion cells (ipRGCs). The strength of the activation of the ipRGCs depends on the magnitude of the difference in S vs (L+M) cone activation between the two light sources. The light sources are equipped with WIFI controlled computers that are programmed to adjust the magnitude of the difference in S vs (L+M) cone activation between the two modes, and thus activations of ipRGCs, at different times of day. The effect can vary from strong to none as appropriate to maximize the health and happiness of users. For example, strong activation in the morning combats "social jet lag" and stimulates alertness. Strong activation in the middle of the day in the workplace or school can enhance alertness and cognitive capacity. However, weak or no activation in the evening promotes relaxation and undisrupted circadian rhythms. The transition between the two modes can be rendered imperceptible in one of two ways. One way is to keep the quantal catch for the L+M cones constant between the two modes thus only modulating the S-cones in the transition between the two modes. The other way is to keep the quantal catch for (S+M)–L cones silent between the two modes. The most appropriate method depends on the exact details of the spatial, temporal and spectral characteristics of the lights.

Melatonin levels in human saliva are an indication of the body's circadian rhythm. During the day and exposure to sun, melatonin secretion is reduced and at night when the sun has set melatonin secretion increases. Disruption of the one's normal melatonin cycle is an indication of the disruption of one's internal circadian rhythm. Monitoring melatonin levels provides insight into one's circadian rhythm. One aspect of a person's circadian rhythm is the phase of the circadian clock which can be assessed by measuring the dim light melatonin onset (DLMO).

Figure 2A:
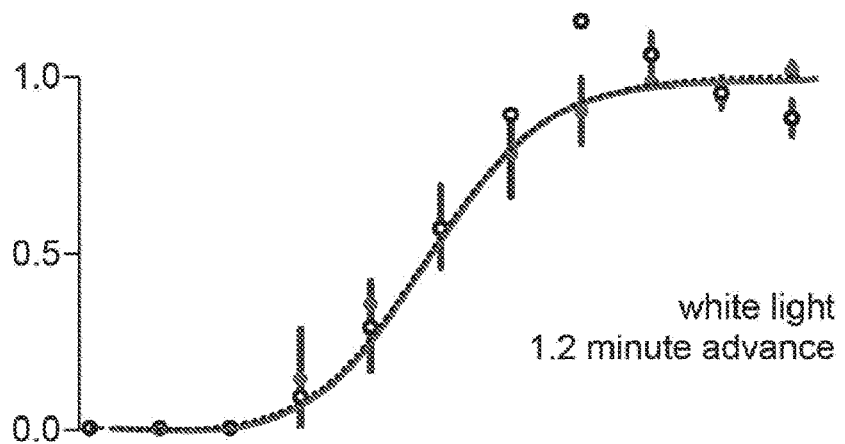
FIGS. 2A-2C compare phase shift effectiveness as measured by saliva melatonin levels as a function of time in individuals in the evening and morning after subject to one hour light exposure.
Figure 2B:
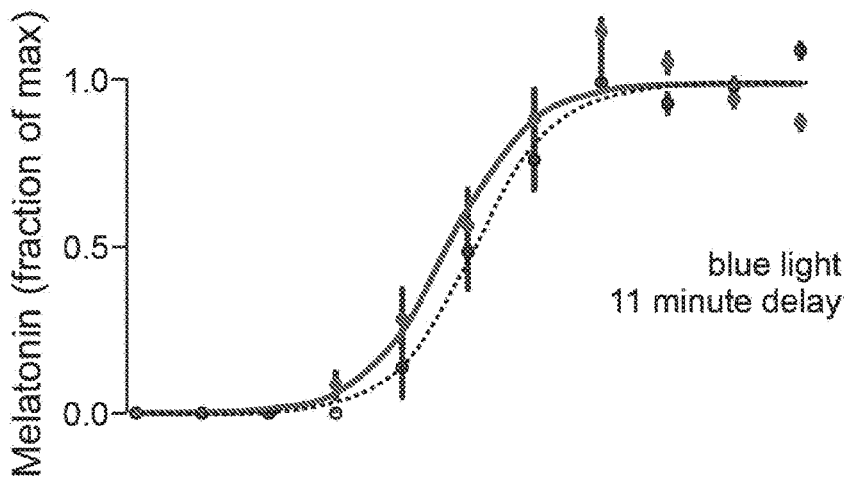
Figure 2C:
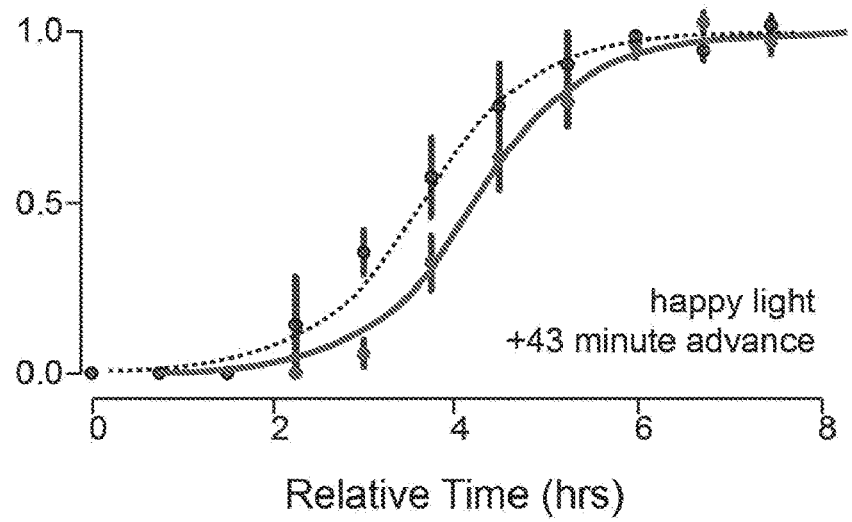

FIGS. 2A-2C compares saliva melatonin levels as a function of time in individuals in the evening and morning after subject to one-hour light exposure (FIG. 2A, white light; FIG. 2B, blue light; FIG. 2C, multi-band light in accordance with the invention).

FIGS. 2A-2C provide a demonstration of the very strong effectiveness of 430, 565 nm vs 485, 565, 630 nm mode alternation against blue light and a stead white light equated in melanoptic lux intensity. Results are the average for 3 subjects (error bars plus & minus one SEM). Shown in all graphs is the rise in saliva melatonin. Evening rise in melatonin secretion is regulated by our internal circadian pacemaker and it is used as an indicator of the phase of the internal clock. This experiment was carried out over three evenings. On the first evening, a baseline melatonin curve was obtained (gray dots and solid lines in FIGS. 2A, 2B, and 2C). The following morning subjects viewed a steady white light for 1 hr (FIG. 2A), a blue light for 1 hr (FIG. 2B), or multi-band light in accordance with the present invention (happy light) for 1 hr (FIGURE C). That evening a second melatonin curve was determined (unfilled circles and black dashed lines in FIGS. 2A, 2B, and 2C). Only a 1.2 minute (non-significant) phase advance was observed in response to a white light stimulus, an 11 minute delay (non-significant)

was observed in response to blue light, and a 43 minute advance (significant) was achieved in response to the 430, 565 nm vs 485, 565, 630 nm mode alternation mode. This phase advance shown in FIG. 2C demonstrates the powerful effects of the multi-band light in accordance of the invention compared to steady white light (FIG. 2A) and blue light (FIG. 2B).

In this experiment, the 430, 565 nm vs 485, 565, 630 nm modes were alternated temporally (alternating at 17 Hz for 1 hr). However, the same effect can be achieved using spatial patterns of 430, 565 nm vs 485, 565, 630 nm lighting elements and viewing the lighting elements or viewing the illumination of surfaces illuminated by the lighting elements with an alternating spatial pattern. Here, 17 Hz was chosen because normal eye movements across the patterned light are expected to produce a virtual temporal alternation on the retina of near 17 Hz. The light used was adjusted to have the same intensity which was defined as having the same time averaged effect on the intrinsic photopigment melanopsin.

Narrow band blue light with peak wavelengths near 480 nm has been shown to be 10-15 times more effective than white light at stimulating cells in the retina responsible for circadian entrainment. However, as demonstrated herein blue light is still relatively ineffective compared to the method of the invention. Moreover, in order to be effective, the blue lights have to narrow band an must be presented in isolation in the absence of exposure to wavelengths outside the narrow band. For example, white lights have blue light as a component but white lights that contain the same amount of blue light as a narrow band blue light that is effective on its own are not themselves effective. Narrow band blue lights cannot be used as standard lighting in home, school, health care or business settings, as can the present invention. The results demonstrate the vast superiority of the invention described here to blue lights designed to influence circadian rhythms.

Importantly, the present invention can be used as standard white lighting in residential, business and healthcare settings. Moreover, the effect on circadian rhythms can be modulated at different times of day to maximize positive effects on health.

FIGS. 3A-3D depict representative embodiments of devices and systems transmitting the select multi-band light in accordance with the methods of the invention.

Figure 3A:
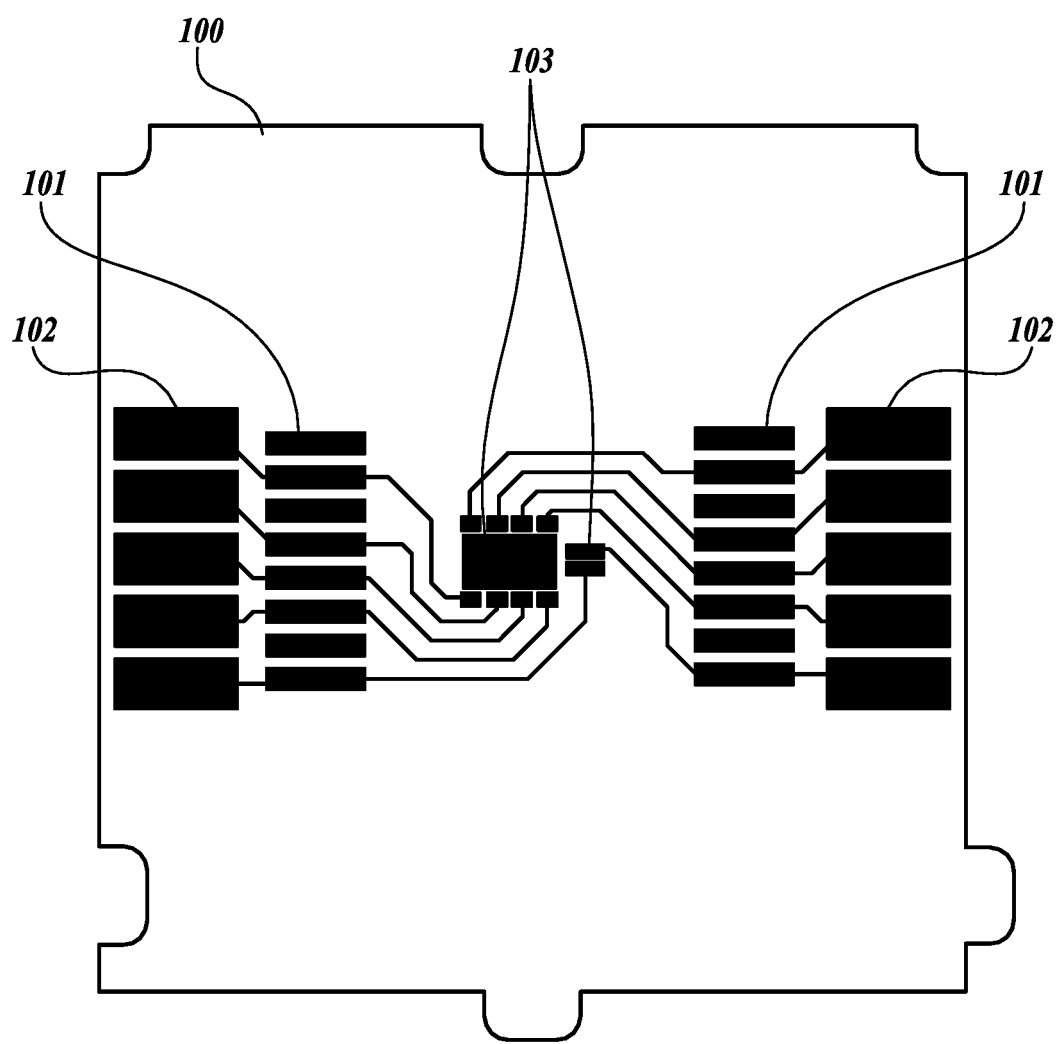
FIGS. 3A-3D depict various aspects of device and system embodiments for a light source for transmitting select narrow bands of light.

FIG. 3A is a schematic illustration of a single lighting element with input/output connections such that an individual lighting element may be configured in series or parallel. Circuitry to control four narrow bands of light then controls intensity of four narrow bands of light with peak wavelengths near 430 nm, 485 nm, 565 nm, and 630 nm. Alternating 430, 565 nm vs. 485, 565, 630 nm modes produces powerful effects on neural circuits in the eye that control circadian rhythms, mood, alertness, and cognitive capacity.

Referring to FIG. 3A, the single lighting element includes circuit board 100 (e.g., aluminum or other material effective at transferring heat away from the digital light emitters) on which are mounted pads 101 and 102 for plastic interconnection (101) or direct soldering (102) to LED packages 103 shown in a typical layout. The single lighting element shown in FIG. 3A contains five individual LED emitters inside two LED packages. The larger LED package (left) is a 4-in-1 LED package containing a red, green, blue, and white LEDs (Cree XLamp XM-L series, part number XMLCTW-A2-0000-00C2AAAB1 from Cree). The smaller LED package (right) is a single LED emitter package containing a violet LED (Lumiled Luxeon UV U2 series manufacturer part number L1F3-U410200014000 from Luxeon).

Figure 3B:
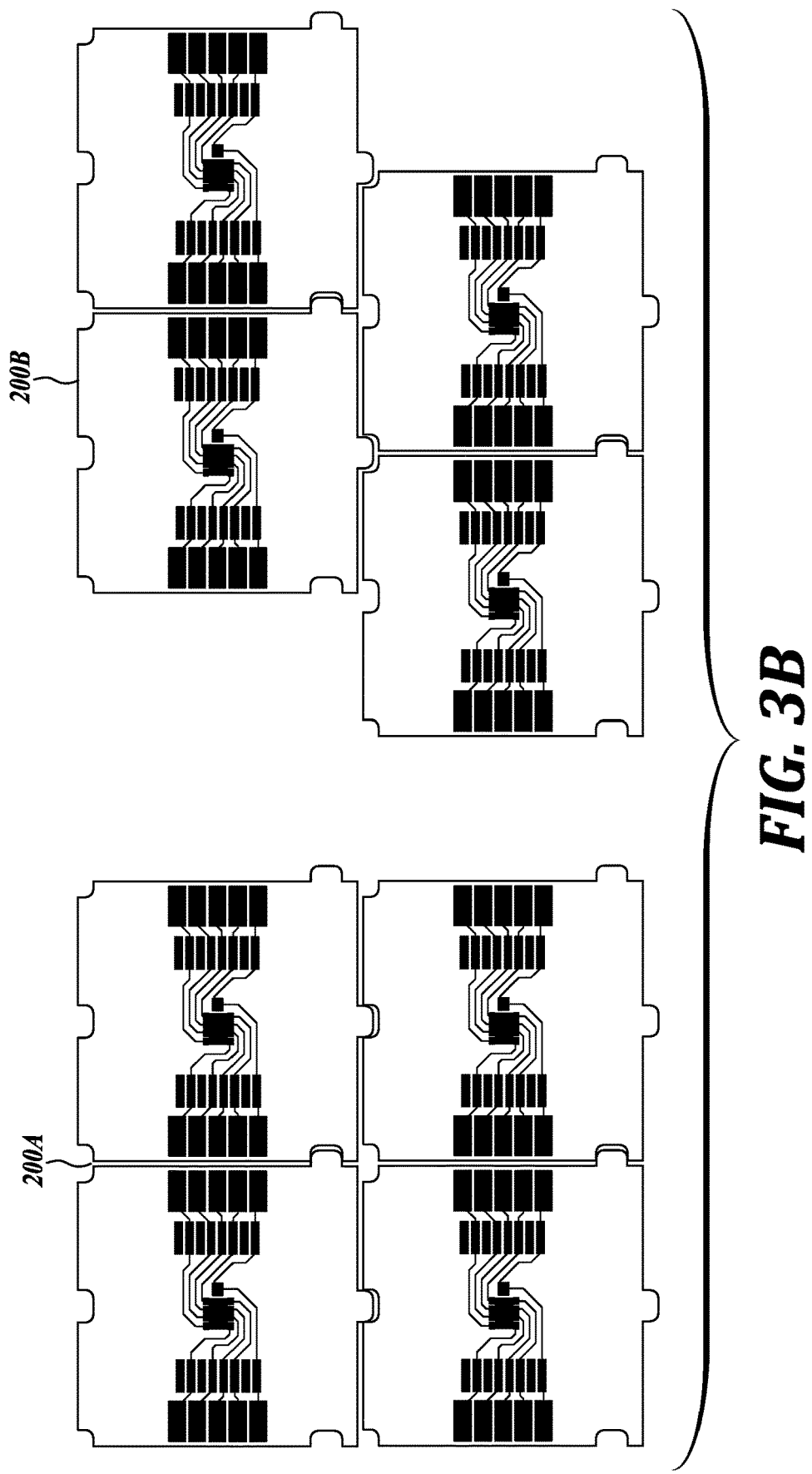

FIG. 3B illustrates two configurations of four single lighting elements, where a single lighting element consists of multiple LED emitters from the center of an aluminum heat sink: a vertical checkerboard ("even") configuration (200A) and an offset ("odd") configuration (200B). The representative systems combine individual lighting elements to create array structures to provide representative lighting panels of desired shapes and sizes that can be configured to conform to current lighting in residential, school, business, and medical settings.

Figure 3C:
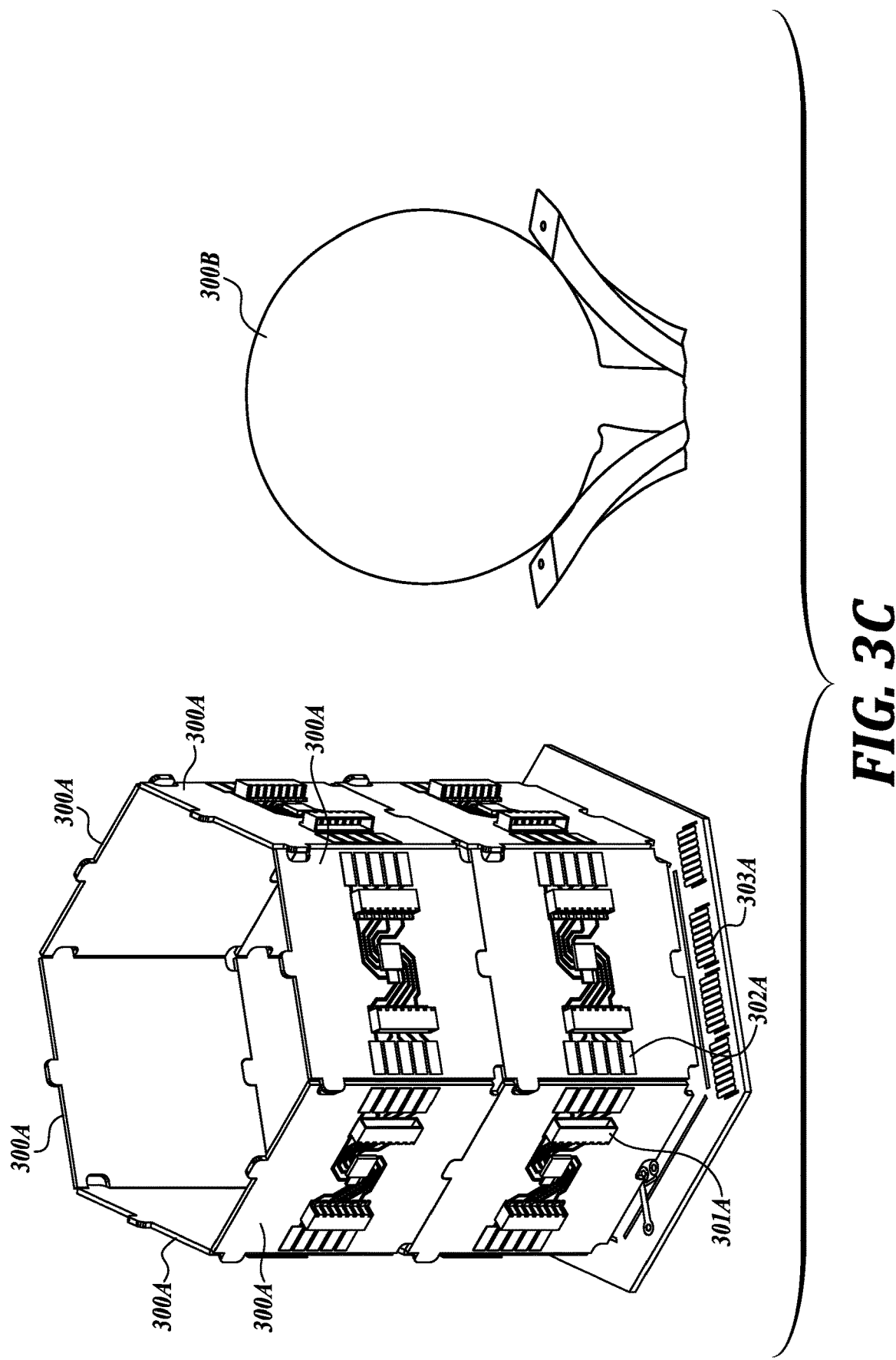

FIG. 3C illustrates a representative configuration of lighting elements combined in a cylindrical hexagonal shape (left) for integration into a lighting fixture having a spherical shape (right image) that can be used as a table or floor lamp. Other arrays may be configured to suit use in fixed indoor lighting systems, wearable devices, or aircraft cabin lighting.

Referring to FIG. 3C, configuration 300A includes six individual lighting elements forming the upper row of a hexagonal shape in a lamp implementation (and six individual lighting elements forming the lower row of a hexagonal shape in a lamp implementation) (each upper row lighting element shown as 300A). Interconnect 301A (plastic) provides an electrical connection with the individual LEDs and LED driver board 303A drives the individual LED wavelengths. This hexagonal configuration of driver circuitry and spatial LED arrangement can be positioned inside spherically-shaped glass diffuser 300B to provide a lamp emitting light perceived by the human eye as white light.

Figure 3D:
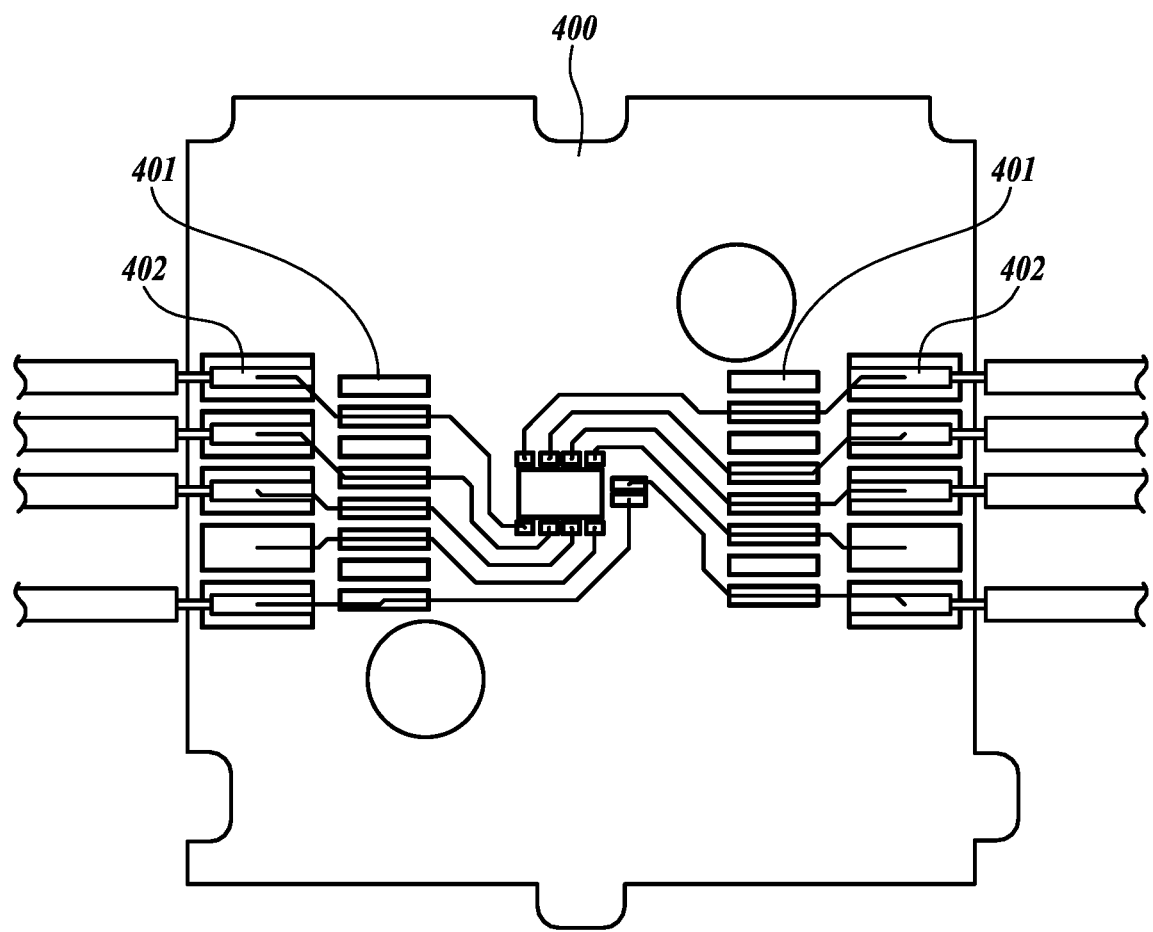

FIG. 3D is an illustration of a single lighting element located at the center of a circuit board for dissipating heat. For reference, the area of a single lighting element as shown is about 40 mm by 40 mm, though this embodiment's design may be adapted to suit other installments.

Referring to FIG. 3D, single lighting element 400 with LED connections made via soldered wires 401 on pads 402. In this embodiment, plastic interconnects were not used in favor of direct solder pads. As shown in FIG. 3A, element 400 includes two LED packages: the left LED package contains four LEDs in one package, and the right LED package contains one LED.

As used herein, the "about" refers to ±5% of the specified value.

While illustrative embodiments have been illustrated and described, it will be appreciated that various changes can be made therein without departing from the spirit and scope of the invention.

The embodiments of the invention in which an exclusive property or privilege is claimed are defined as follows:

1. A lighting device, comprising two light sources:
   (a) a first light source that emits a first band of light having a bandwidth from about 410 nm to about 450 nm; and
   (b) a second light source that emits a second band of light having a bandwidth from about 545 nm to about 585 nm,
   wherein the lighting device does not emit light at a wavelength other than from about 410 nm to about 450 nm and from about 545 nm to about 585 nm.

2. The lighting device of claim 1, wherein the first and second bands of light are emitted from a single point source.

3. The lighting device of claim 1, wherein the lighting device has a luminosity flux from about 200 to about 5000 lumens.

4. The lighting device of claim 1, wherein the first light source emits a first band of light having a peak emission at 430 nm.

5. The lighting device of claim 1, wherein the second light source emits a second band of light having a peak emission at 565 nm.

6. A lighting system, comprising one or more lighting devices of claim 1.

7. A method for selectively activating S cones and L+M cones in a human retina using the lighting device of claim 1.

8. The method of claim 7, wherein the S cones are activated by the first light source.

9. The method of claim 7, wherein the L+M cones are activated by the second light source.

10. A method for regulating the phase of circadian rhythm in a subject using the lighting device of claim 1.

11. A lighting device that emits (i) a first band of light having a bandwidth from about 410 nm to about 450 nm and (ii) a second band of light having a bandwidth from about 545 nm to about 585 nm, wherein the lighting device does not emit light at a wavelength other than from about 410 nm to about 450 nm and from about 545 nm to about 585 nm.

12. A lighting system, comprising:
(a) one or more first lighting devices that emit light having a bandwidth from about 410 nm to about 450 nm; and
(b) one or more second lighting devices that emit light having a bandwidth from about 545 nm to about 585 nm,
wherein the lighting system does not include a lighting device that emits light at a wavelength other than from about 410 nm to about 450 nm and from about 545 nm to about 585 nm.

13. The lighting system of claim 12, comprising about the same number of first lighting devices and second lighting devices.

14. The lighting system of claim 12, wherein the system is deployed in a low natural light environment.

* * * * *